(12) United States Patent
Tanaka et al.

(10) Patent No.: US 8,221,997 B2
(45) Date of Patent: *Jul. 17, 2012

(54) MICROORGANISM AND METHOD FOR PRODUCING CAROTENOID USING THE SAME

(75) Inventors: Toru Tanaka, Kawasaki (JP); Teruhiko Ide, Hachioji (JP); Kei-ichi Murayama, Yamamoto (JP); Seigou Oe, Yokohama (JP); Toru Imaizumi, Sagamihara (JP); Satoshi Hanzawa, Ebana (JP); Toshinobu Toyoshima, Sagamihara (JP)

(73) Assignee: Tosoh Corporation, Shunan-shi (JP)

( * ) Notice: Subject to any disclaimer, the term of this patent is extended or adjusted under 35 U.S.C. 154(b) by 1017 days.

This patent is subject to a terminal disclaimer.

(21) Appl. No.: 12/089,451

(22) PCT Filed: Sep. 26, 2006

(86) PCT No.: PCT/JP2006/319031
§ 371 (c)(1),
(2), (4) Date: Jun. 5, 2008

(87) PCT Pub. No.: WO2007/049421
PCT Pub. Date: May 3, 2007

(65) Prior Publication Data
US 2009/0221026 A1    Sep. 3, 2009

(30) Foreign Application Priority Data

Oct. 28, 2005  (JP) ................................ 2005-314667
Dec. 5, 2005   (JP) ................................ 2005-350225

(51) Int. Cl.
C12P 23/00    (2006.01)
C12N 1/20     (2006.01)
C12N 1/38     (2006.01)

(52) U.S. Cl. ........................ 435/67; 435/244; 435/252.1

(58) Field of Classification Search ........................ None
See application file for complete search history.

(56) References Cited

FOREIGN PATENT DOCUMENTS

| JP | 2001 352995 | 12/2001 |
| JP | 2005-58216 | 3/2005 |
| JP | 2005 58216 | 3/2005 |
| WO | 92 21764 | 12/1992 |
| WO | 99/06586 | 2/1999 |

OTHER PUBLICATIONS

Selection of Astaxanthin-overproducing mutants of *Phaffia rhodozyma* with beta ionon Appl Environmental Microbiol. Sep. 1990. 56(9) 2944-2945.*
U.S. Appl. No. 12/089,486, filed Apr. 7, 2008, Ide, et al.
Lewis, M. J. et al., "Selection of Astaxanthin-Overproducing Mutants of *Phaffia rhodozyma* with beta-Ionone", Applied and Environmental Microbiology, vol. 56, No. 9, pp. 2944-2945, (1990).
Yamane, Tsuneo "Bio Process System Engineering", Kabushiki Kaisha CMC, pp. 115-125, (2002).
M. J. Lewis, et al.; "Selection of Astaxanthin-Overproducing Mutants of *Phaffia rhodozyma* with β-Ionone"; Applied and Environmental Microbiology; Sep. 1990; vol. 56; No. 9; XP003011631; pp. 2944-2945.
Office Action issued Jan. 31, 2012, in Japanese Patent Application No. 2006-227799.
Tsuneo Yamane, "Bio Process System Engineering", Kabushiki Kaisha CMC, Nov. 30, 2002, pp. 115-125 (reference previously filed on May 8, 2008, submitting complete copy).

* cited by examiner

*Primary Examiner* — Kagnew H Gebreyesus
(74) *Attorney, Agent, or Firm* — Oblon, Spivak, McClelland, Maier & Neustadt, L.L.P.

(57) ABSTRACT

To provide a microorganism capable of producing a large amount of carotenoids, mainly astaxanthin, and to provide a method of producing carotenoids using the microorganism, a microorganism having improved carotenoid productivity is used, which is obtainable by breeding a carotenoid producing *Paracoccus* bacteria which is featured by producing 720 mg or more carotenoid per 1 L of culture medium. Also used is a method of producing carotenoids using the bacterium.

10 Claims, 8 Drawing Sheets

FIG.1

At 144 hours of culture

Total carotenoid amount   31.5mg/L

Astaxanthin               17.4mg/L

FIG.2

At 168 hours of culture

Total carotenoid amount   30.6mg/L

Astaxanthin   20.9mg/L

MICROORGANISM AND METHOD FOR PRODUCING CAROTENOID USING THE SAME

CROSS-REFERENCE TO RELATED APPLICATIONS

The present application is a 35 U.S.C. §371 National Stage patent application of International patent application PCT/JP2006/319031, filed on Sep. 26, 2006, which claims priority to Japanese patent applications JP 2005-350225, filed on Dec. 5, 2005 and JP 2005-314667, filed on Oct. 28, 2005.

TECHNICAL FIELD

The present invention relates to a novel microorganism and a method of producing carotenoids, in particular, astaxanthin using the same.

BACKGROUND ART

Astaxanthin is a compound that is conventionally used for reviving the colors of farm-raised fish such as salmon, trout, and sea bream, and recently considered about application to health food owing to its antioxidant activity. Astaxanthin is obtainable from natural products by extraction from crustaceans such as south pole euphausiid or culturing of yeast, microalgae and the like, however, nowadays chemically synthesized astaxanthin is widely used on account of stability of supply and cost problems. However, since chemically synthesized astaxanthin is susceptible to contamination of impurities from the process, particularly, of deleterious substances used in synthesis reaction, provision of natural products is demanded from the view point of safety. On the other hand, naturally occurring astaxanthin suffers from the problems in stability of supply and cost, and astaxanthin obtained by culturing of yeast or microalgae, in particular, faces a problem of contamination of fatty acid ester as a byproduct. Also it faces a problem that complicated process should be taken for extraction because of rigid cell walls.

For improving this, Japanese Patent Laid-Open Publication No. Hei 7-184668 (referred to as Patent Document 1) discloses a production method based on culturing of marine bacteria belonging to a genus *Agrobacterium* (for example, strain N-81106 (deposition number: FERM P-14023) later reclassified into bacteria belonging to *Paracoccus*, see Non-patent documents 1, 2 and 3). The invention is advantageous in that astaxanthin can be easily obtained only by mixing and stirring an organic solvent such as acetone and bacterial cells after harvesting cultured cells of marine bacteria. However, the astaxanthin obtained by culturing the above bacterium is as small as about 0.1 mg per 1 litter of culture solution, so that improvement in production amount is desired. Regarding a production process of astaxanthin based on culturing of bacteria, description can be found in Japanese Patent Laid-Open Publication No. 2001-352995 (referred to as Patent document 2) about a production method using soil bacteria, wherein 128 mg per 1 litter is produced. However, for use in aquafarming of marine products such as trout and sea bream, it would be preferable to use a microorganism obtained from the environment in which the marine product grows from the view point of safety. Therefore, improvement in production process by such marine microorganisms is desired.

In order to solve these problems, one conventional art reports conducting mutation breeding by using a marine bacterium strain N-81106, belonging to a genus *Agrobacterium* (deposition number: FERM P-14023) to acquire strain TSUG1C11 (deposition number: FERM P-19416) that produces 19.4 mg of astaxanthin per 1 litter of culture solution (see Patent document 3). It also reports acquisition of strain TSN18E7 (deposition number: FERM P-19746) that produces 200 mg of astaxanthin and 400 mg of total carotenoid per 1 litter of culture solution through further mutation breeding (see Patent document 3). From the viewpoint of industrial production, however, it is desired to produce more carotenoids such as astaxanthin, and hence strains having improved productivity are desired.

In industrial culturing of microorganisms, in particular, culturing of *Escherichia coli* or yeast, it is known that objective substances or microbial cells can be obtained at higher yield by a fed-batch culture method in which components of culture medium are supplemented during culture, than by a batch culture method in which necessary nutrients are loaded at once. Here, supplementing ingredients of culture medium is called "feeding". With the feeding culture, nutrients to be supplemented can be desirably controlled, usually to lower concentrations. When production of objective substances or growth is prevented or when a byproduct such as alcohol and organic acid is produced by high concentration of substrates, such phenomenon can be suppressed by the control as described above. Particularly well known are suppression of production of objective substances, called "catabolite repression" observed when concentration of saccharides such as glucose in ingredients of culture medium is high, and suppression of growth of microorganism caused by toxicity of methanol and the like alcohols used at concentration. It is also known that when glucose is used at high concentration, ethanol and acetic acid accumulate for the case of yeast and *Escherichia coli*, respectively, and when they exceed 20 g/L and 5 g/L, respectively, growth is suppressed by byproducts. Production of byproducts is unfavorable because it not only suppresses growth but also deteriorates quality of objective substance and makes purification difficult. However, these findings are for phenomena observed mainly in culturing of *Escherichia coli* and yeast, and there is no finding about the effect of concentration of nutrient in carotenoid producing microorganisms which are objectives of the present invention. As a subject nutrient, saccharides and the like carbon sources which are greatly consumed can be exemplified. However, since the consumption rate varies depending on the growth condition of microorganism, in order to keep the concentration of carbon source constant during culturing, it is necessary to control the feeding amount while monitoring the growth condition of microorganism by an appropriate means. Various proposals have been made to achieve this. For example, a method of feeding carbon source is known which uses consumption of oxygen as an index. According to this method, consumption of oxygen is determined from a difference in oxygen level between inlet gas and outlet gas. However, since measurement of oxygen concentration contains relatively great error and has a drawback of slow response, microbial activity during culture cannot be estimated accurately. This makes it difficult to control when an unexpected change occurs. As a method based on an analysis of composition of outlet gas, a method in which feeding is executed while taking respiration quotient (RQ) as an index is also known. Respiration quotient is an index that shows a ratio of fermentation and respiration in culturing of yeast, for example, and advantageously reflects metabolism condition of microorganism (see, for example, Non-patent document 4). As to microorganisms other than yeast, however, the efficacy is not clear. Respiration quotient is calculated from differences in oxygen concentration and carbon dioxide gas concentration between inlet gas and outlet gas. Therefore, not only there arises a problem concerning oxygen concentration measurement as described above, but also there arises a need for calculation based on two index measurements of oxygen concentration and carbon dioxide concentration, making data processing relatively complicated.

Also known is a method which uses change in pH or change in dissolved oxygen (DO) as a physicochemical index, however, such method has a problem of low response speed of a sensor, and faces a problem that in the case of carbon source depletion, a stress due to the depletion occurs to cause change in biological metabolic activity because of the slow response to compensation for the depletion. A method using an on-line glucose analyzer is disadvantageous in long-term stable control because of influences of required sampling amount, analyzing time, accuracy, stability, liquidity and the like. A method using an on-line laser turbidity meter is disadvantageous in that accuracy is deteriorated when the density of bacterial cells is high (see, for example, Non-patent document 5).

In view of the above, not only proposal of a new method is demanded, but also there is a problem that efficacy of the above indexes on carotenoid producing bacteria which are subjects of the present invention is not known at all because the above methods are developed for yeast, *Escherichia coli* and the like.

[Patent document 1] Japanese Patent Laid-Open Publication No. Hei 7-184668
[Patent document 2] Japanese Patent Laid-Open Publication No. 2001-352995
[Patent document 3] Japanese Patent Laid-Open Publication No. 2005-58216
[Non-patent document 1] Internet (website of Marine Biotechnology Institute), Biotechnology Institute, MBIC (cell strain collection database), [online], date of published unknown, sections of "characteristics", "strain name" and "16s" in page 9, [found by a search on Jun. 8, 2005], Internet
[Non-patent document 2] Internet (website of National Institute of Genetics, JAPAN) Research Organization of Information and Systems National Institute of Genetics, Japan DNA databank, "DNA Data Bank of Japan", [online], Oct. 8, 2002, page 3, section of "ORIGIN", [found by a search on Jun. 8, 2005], Internet
[Non-patent document 3] Internet (website of US National Institute of Health), National Institute of Health, National Center for Biotechnology Information, [online], Oct. 8, 2002, page 4, sections of "Source origin" and "Features, [found by a search on Oct. 18, 2005], Internet
[Non-patent document 4] Murayama and Takemoto, TOSOH Research report, No. 28, pp. 49-58, 1984.
[Non-patent document 5] Yamane, T et al., J. of Ferment. Bioeng., 75, 443, 1993

DISCLOSURE OF THE INVENTION

Means to be Solved by the Invention

It is an object of the present invention to provide a marine microorganism capable of producing a large amount of carotenoids, mainly astaxanthin, and to provide a method of producing carotenoids and/or astaxanthin using the microorganism.

Means for Solving the Problem

Through diligent efforts, inventors of the present invention achieved the present invention. Specifically, the present invention concerns a bacterium belonging to a genus *Paracoccus* having improved productivity of carotenoid by virtue of increased density of bacterial cells, which is obtained by breeding of carotenoid producing bacteria belonging to a genus *Paracoccus*. Also the present invention concerns a method of producing carotenoid including culturing such a bacterium and collecting carotenoid from bacterial cells or a culture solution. To be more specific, the present invention relates to the followings.

(1) A microorganism having improved carotenoid productivity, which is obtainable by breeding a carotenoid producing bacteria belonging to a genus *Paracoccus* which is featured by producing 720 mg or more carotenoid per 1 L of culture medium. (2) A microorganism having improved carotenoid productivity, which is obtainable by breeding a carotenoid producing bacteria belonging to a genus *Paracoccus* which is featured by producing 250 mg or more astaxanthin per 1 L of culture medium.

(3) The microorganism according to (1) or (2), wherein the microorganism is a carotenoid producing bacterium, *Paracoccus* sp. strain TSTT052 (deposition number: FERM P-20690).

(4) A method of producing carotenoids by culturing a microorganism having productivity of carotenoids, while keeping a concentration of carbon source in a culture solution containing the microorganism at a low concentration.

(5) The method of producing carotenoids according to (4), wherein the microorganism is a bacterium, *Paracoccus* sp. strain N-81106 or a mutant strain thereof.

(6) The method of producing carotenoids according to (4) or (5), wherein the mutant strain is a strain TSTT052 (deposition number: FERM P-20690).

(7) The method of producing carotenoids according to any one of (4) to (6), wherein a concentration of carbon source in the culture solution is kept at 10 g/L or less.

(8) The method of producing carotenoids according to any one of (4) to (7), wherein the concentration of carbon source in the culture solution is kept at such a concentration that does not cause depletion of carbon source in any stages of culturing.

(9) The method of producing carotenoids according to (8), wherein depletion of carbon source occurs at a concentration of carbon source of 0 g/L, and is a condition that is associated with deterioration of respiration activity of the microorganism being cultured.

(10) The method of producing carotenoids according to any one of (4) to (9), wherein an amount of carbon dioxide gas generating from the culture solution is measured, and a feeding amount of carbon source is controlled based on the measurement to keep the concentration of carbon source in the culture solution.

(11) The method of producing carotenoids according to any one of (4) to (10), wherein the concentration of carbon source in the culture solution is controlled so that an amount of carbon dioxide gas generating from the culture solution is proportion to a feeding amount of carbon source to the culture solution.

(12) A mutant strain of carotenoid producing microorganism that exhibits resistance against a compound which is a metabolic analogue of a carotenoid compound and inhibits growth.

(13) A method of producing a carotenoid using the microorganism according to (12).

(14) A method of breeding a carotenoid producing microorganism with the use of a metabolic analogue of a carotenoid compound.

(15) The method of breeding according to (14), wherein a growth ability of the carotenoid producing microorganism is improved.

Effect of the Invention

With the novel microorganism of the present invention, it becomes possible to efficiently produce carotenoids such as astaxanthin which are useful as color reviving feed for farm-raised fish.

BEST MODE FOR CARRYING OUT THE INVENTION

The novel microorganism with improved carotenoid productivity according to the present invention is a microorganism having improved carotenoid productivity, which is obtainable by breeding a carotenoid producing bacterium, Paracoccus sp. strain TSN18E7 featured by producing 720 mg or more carotenoid per 1 L of culture medium, or a microorganism having improved carotenoid productivity, which is obtainable by breeding of carotenoid producing bacterium Paracoccus sp. strain TSN18E7 featured by producing 250 mg or more astaxanthin per 1 L of culture medium.

More specifically, the novel microorganism with improved carotenoid productivity is a carotenoid producing bacterium Paracoccus sp. strain TSTT001 (deposited to International Patent Organism Depositary, deposition number: FERM P-20670). Further, in the present invention, it is a strain TSTT031 (deposited to International Patent Organism Depositary, deposition number: FERM P-20689) or a strain TSTT052 (deposited to International Patent Organism Depositary, deposition number: FERM P-20690) which is a mutant from strain TSTT001 having improved carotenoid productivity. The microorganism of the present invention is a novel microorganism that is derived through further breeding from bacterium Paracoccus sp. strain TSN18E7 that is derived through breeding from a marine bacterium strain N-81106 which classified into genus Agrobacterium (later, reclassified into bacteria belonging to Paracoccus). Strain N-81106 is a microorganism that is discovered by Marine Biotechnology Institute, and deposited to International Patent Organism Depositary under the deposition number of FERM P-14023. Strain N-81106 is known to accumulate astaxanthin as major carotenoid in cells, as well as other various carotenoids such as β-carotene, β-cryptoxanthin, 3-hydroxyequinenone, canthaxanthin, 3'-hydroxyechinenone, cis-adonixanthin, adonirubin, and adonixanthin (see, for example, Yokoyama and Miki (1995), FEMS Microbiology Letters, 128, pp. 139-144).

The microorganism of the present invention is derived through breeding of bacterium Paracoccus sp. strain TSN18E7. As a method of breeding, various methods can be employed including a method in which bacterial strains with improved productivity is selected after acceleration of mutation by treatment of cells with a mutagenic substance or UV ray, and a method involving cell fusion between bacterial strains having different properties obtained in various manners as described above, in addition to a method of screening excellent bacterial strains derived by natural mutation. The method of using a mutagenic substance is particularly preferred as a method of obtaining a useful strain in short time. As a mutagenic substance, N-methyl-N'-nitro-N-nitrosoguanidine, ethyl methane sulfonate, and the like compounds are preferably used.

In one exemplary method of breeding, bacterial cells of Paracoccus sp. strain TSN18E7 that are obtained in advance by culturing are suspended in an aqueous solution of a compound as recited above as a mutagenic substance and left for a certain time, and then bacterial cells are collected by centrifugation, for example, to remove the mutagenic substance. Then the cells are cultured on a plate culture medium, followed by selection of colonies of excellent bacterial strains. Colonies with dark color tone are selected and isolated, which are then liquid-cultured. Then from the bacterial cells, carotenoids are extracted, and a generation amount and composition of the carotenoids is analyzed by HPLC or the like to narrow down bacterial strains with improved productivity, whereby excellent bacterial strains are obtained.

However, when mutation is induced at random using chemicals as described above, undesired mutation may be introduced whenever breeding of bacterial strain is conducted to deteriorate growth ability of the bacterium. On the other hand, repeated mutation breeding may also deteriorate growth ability because intracellular production of carotenoids is excess and excess control occurs. These phenomena are undesirable from the view point of fermentation production. The present inventors found that a carotenoid producing bacterial strain having a similar or improved growth ability compared to a parent strain is obtained by adding a predetermined amount of metabolic analogue which is a structural analogue of carotenoid on a plate culture medium for separation of mutant strain used for breeding. In other words, as a result of addition of a metabolic analogue on a plate culture medium, the bacterial strains spread on the culture medium incorporate the metabolic analogue into cells. This provides an environment which is comparable to the environment in which carotenoids highly accumulate, so that most of bacterial strains reduce growth ability and fail to form colonies. On the other hand, a strain that is resistant to a metabolic analogue of carotenoids and forms colonies is a bacterial strain capable of growing well even when a certain amount of carotenoids accumulates in the cell.

Generally in microorganisms, when more than a certain amount of metabolic substance is produced, the substance is regulated, for example, by feedback, and the substance is disabled from further production. This is because substances constituting a cell are coordinated in their respective amounts. In this respect, breeding of microorganisms intended for improvement of productivity of a specified substance, for example, is a treatment that disturbs the intracellular coordination. In other words, repetition of breeding causes significant improvement of synthetic ability of an objective substance, and continuous production of the objective substance in an amount exceeding a predetermined amount may cause remarkable reduction in growth ability of the microorganism. One measure for clearing such a mechanism is to isolate a metabolic analogue resistant strain which grows in the presence of metabolic analogue.

As a microorganism by which metabolic analogue resistance is to be acquired, any microorganisms whose growth is inhibited by such a carotenoid metabolic analogue is available, and as such, bacteria belonging to Paracoccus are exemplified.

As a metabolic analogue, those being analogous to carotenoids, such as α-ionone, β-ionone, and the like can be exemplified. The concentration added to a plate culture medium may be appropriately determined through a growth inhibitory test or the like on the microorganism to be bred. The final concentration is preferably 0.01 to 1000 mM and more preferably from 1 to 10 mM.

In the present invention, an excellent bacterial strain may be determined by evaluating an appropriate bacterial strain. When a solid culture medium is used, evaluation may be achieved by picking up an arbitrary colony and subjecting it to liquid culture, and evaluating growth ability and productivity of carotenoids.

Microorganisms used in the methods of the present invention may be cultured in any nutrient culture media well known in the art. Bacterial strains used in a culturing step may be transferred to a fermentation tank from a streak culture plate according to a known method. Preferred methods are methods using an agar plate medium, an agar slant medium, and a flask culture solution.

As a culture medium used in the present invention, any culture media may be used as far as the bacterium is able to grow and produce carotenoids therein. As a carbon source, molasses, glucose, fructose, maltose, sucrose, starch, lactose, glycerol, acetic acid, and the like; as a nitrogen source, natural ingredients such as corn steep liquor, peptone, yeast extract, meat extract and soybean cake, ammonium salts such as ammonium acetate, ammonium chloride and ammonium sulfate, amino acids such as glutamic acid, aspartic acid, glycine, and the like; as an inorganic salt, sodium phosphate, disodium phosphate, potassium phosphate, dipotassium phosphate, and the like phosphate salts, and sodium chloride; as a metallic ion, magnesium chloride, magnesium sulfate, ferrous sulfate, ferric sulfate, ferrous chloride, ferric chloride, iron citrate, ammonium ferric sulfate, calcium chloride dihydrate, calcium sulfate, zinc sulfate, zinc chloride, copper chloride, manganese chloride, and the like; and as vitamins, yeast extract, biotin, nicotinic acid, thiamine, riboflavin, inositol, pyridoxine, and the like can be used.

As to a culturing condition of a novel microorganism under the condition that allows production of carotenoids such as astaxanthin according to the present invention, any commonly used methods can be applied. In a preferred embodiment of the present invention, culturing is preferably executed in a culture solution. With regard to the liquid culture, conditions that are usually used in liquid culture may be used. Preferably, fermentation lasts for 20 hours to 200 hours at a culturing temperature of 10 to 35° C. and pH of culture medium of 6 to 9. As to the culture temperature, the temperature may be changed among an early stage, a medium stage, and a later stage of culture. Optimum condition using the nutrient culture medium of the present invention is: culture temperature of 20 to 28° C., pH of about 7.0, and culture time of 50 to 150 hours.

In culturing of the present microorganism, by keeping a low sugar concentration which will not cause depletion, growth inhibition of microorganism and production of byproducts such as organic acids are prevented, so that carotenoids are desirably produced. In control of a feeding amount, by adjusting the feeding amount in proportion to an amount of carbon dioxide gas generated by aspiration of microorganism, it is possible to readily keep a carbon source in the culture solution at a low concentration while preventing depletion.

In the present invention, since culturing is executed while keeping a carbon source concentration at low level in a culture solution containing a microorganism, culturing is started with a desired concentration of the ingredients such as carbon source as described above, and after intended concentrations is achieved as a result of consumption by growth of microorganism, a high concentration solution which is separately prepared is fed to the culture solution by means of a pump or the like. When glucose is used as a carbon source, a preferred starting concentration is 0 to 20 g/L, and a concentration of a glucose solution to be fed is preferably high for preventing increase in liquid level of the culture solution, and a solution of 300 to 900 g/L is used.

Concentration of carbon source during culture is controlled to an intended concentration by feeding a solution to be fed into a culture solution according to the feeding formula (1) below.

$$F = A \times f \times (C_{CO2out} - C_{CO2in}) \qquad (1)$$

In the formula (1), "F" represents feeding rate of carbon source (unit: g/min). The value of "A" is coefficient (unit: g/L) and is a constant that is selected depending on the type of fermentation tank or gas analyzer for use, and the type and growth condition of microorganism. The constant is preferably changed to an appropriate value depending on the growth condition of microorganism based on a value determined in an exploratory experiment. Generally, the constant is high in an initial stage of culturing, and low in a later stage of culturing. "f" denotes an aeration amount supplied to a fermentation tank (unit: L/min), and a value of aeration amount f representing flow rate per one minute of air can also be set arbitrarily, however, usually 0.1 to 5.0 VVM (0.1 to 5.0 L/min per 1 L of culture solution) is preferably used. $C_{CO2out}$ represents concentration of carbon dioxide in outlet gas (unit: % by volume), and $C_{CO2in}$ in represents concentration of carbon dioxide in inlet gas (unit: % by volume).

In the present invention, the concentration of carbon source in a culture solution is kept low, and preferably, the target concentration controlled by feeding is set so as not to cause depletion of carbon source and not to exceed 10 g/L, and is preferably 6 g/L or less. Culturing at a carbon source concentration of higher than 10 g/L is not only undesired because organic acid may generate as a byproduct and enter objective carotenoids to deteriorate the quality, but also likely to suppress growth of microorganism and production of carotenoids in the case of accumulation of large quantity. Concentrations exceeding 100 g/L, in particular, significantly inhibit growth and production of carotenoids.

Influence of depletion of carbon source differs depending on the type and growth condition of microorganism. In culturing of carotenoid producing bacteria, depletion occurring in early to middle stage of culturing may possibly inhibit growth and carotenoid production. Also the duration in which depletion lasts has some influence. Depletion of several minutes will not have large influence, however, when the condition in which DO is increased due to depletion lasts over 10 minutes, production of carotenoid will be suppressed.

Occurrence of depletion may be checked, but not limited, by decrease in aeration activity. Decrease in aeration activity appears, for example, in the form of increase in dissolved oxygen concentration (DO) of culture solution, increase in oxygen concentration and decrease in carbon dioxide gas concentration in outlet gas, or increase in pH. DO is a particularly preferred index. This is because depletion of carbon source causes deterioration in aeration activity of microorganism and rapid increase in DO, although DO is kept at a level lower than the oxygen saturation concentration because oxygen is consumed by aeration of microorganism when an adequate concentration of carbon source is maintained.

In order to prevent depletion, carbon source may be added in coordination with rapid increase of DO. When composition of outlet gas or pH is used as an index for depletion, the response tends to be slow compared to the cases using DO as an index, so that some attention should be paid. Here, even when the carbon source concentration is 0 g/L, it is not a depletion condition unless aeration activity is deteriorated. Such a case occurs when consumption rate by bacterium matches with feeding rate of carbon source. In such a case, even when the carbon source concentration is 0 g/L, carbon source required for maintaining metabolic condition of microorganism is supplied, and growth and carotenoid production proceed satisfactorily.

In the present invention, it is possible to efficiently produce carotenoids by measuring an amount of carbon dioxide gas generating from a culture solution, and controlling a feeding amount of carbon source based on the measurement to keep the carbon source concentration in the culture solution.

The method of analyzing carbon dioxide gas concentration which is used as an index for feeding of carbon source is not particularly limited, and a commercially available outlet gas analyzer for culturing devices, for example, may be used for measurement of an amount of carbon dioxide gas generating from the culture solution.

For controlling a feeding amount of carbon source based on the measurement of carbon dioxide gas amount generating from the culture solution, for example, a controlling method is exemplified which uses a variety of devices for data processing and transfers a carbon dioxide gas amount measurement signal received by the data processing device to a feeding pump as a signal determining a feeding amount based on an appropriate control formula.

More specifically, a device capable of transferring data to a data processing device such as a personal computer for the purpose of increasing efficiency of data processing can be exemplified, and a method of controlling feeding amount of carbon source is not particularly limited. Furthermore, based on an analytical value of carbon dioxide gas concentration in outlet gas, an appropriate feeding amount may be calculated as desired according to the formula (1) as described above, and a carbon source may be continuously supplied while adjusting the flow rate of the feeding pump. Furthermore, control may be given so that an average feeding amount in an arbitrarily set period time matches with an objective feeding rate determined by the formula (1) by causing a pump set at a constant flow rate operate intermittently. For example, a method of controlling carbon source concentration in the culture solution by setting an amount of carbon dioxide gas generating from the culture solution to be in proportion to a feeding amount of carbon source can be exemplified. These controls may be manually executed, or automatically executed via a computer or a special control device.

The method of analyzing carotenoids in the present invention is not particularly limited insofar as stable and efficient collection from bacterial cells or a culture solution is realized, and as a solvent for use in extraction, methanol, ethanol, isopropyl alcohol, acetone, methyl ethyl ketone, methyl isobutyl ketone, dichloromethane, chloroform, dimethyl formamide, and dimethyl sulfoxide can be exemplified. Quantification of extracted carotenoids is preferably conducted by a high performance liquid chromatograph capable of separating various carotenoids, and having excellent quantification ability.

For collecting carotenoids and/or astaxanthin from bacterial cells or a culture solution following culturing, for example, bacterial cells may be separated from a culture solution by a centrifugation or the like and extracted therefrom by an appropriate organic solvent. Examples of such an organic solvent include methanol, ethanol, isopropyl alcohol, acetone, methyl ethyl ketone, methyl isobutyl ketone, dichloromethane, chloroform, dimethyl formamide and dimethyl sulfoxide. Among them acetone is preferred. Further, separation and purification into higher purity may be achieved by utilizing a liquid chromatography or the like. Liquid chromatography may be based on a separation principle of ion exchange, hydrophobic interaction, and molecular sieve, for example. Reverse-phase chromatography and normal-phase chromatography are preferred. Alternatively, extraction from cells may be conducted by supercritical fluid extraction.

Alternatively, after completion of culturing, bacterial cells may be separated from the culture solution by way of centrifugal separation, decantation, or filtration, for example. The obtained bacterial cells are added with water to be rendered a slurry having a convenient viscosity. In order to prevent decomposition of carotenoids such as astaxanthin, an appropriate additive may be added to the slurry. Examples of such an additive include, but are not limited to, antioxidants such as ascorbic acid. Thereafter, the prepared slurry is homogenized with the use of a grinder using glass beads or zirconia beads or high-pressure homogenizer, and dried for use later. A preferred drying method is spry drying.

The bacterial cells may directly be added to feeds for farm-raised fish or the like. Alternatively, they may be extracted from a polar solvent or the like as describe above before use. Cell bodies remaining after extraction of carotenoids such as astaxanthin and containing little pigments can be used as ideal supply sources of proteins and vitamins in poultry raising.

EXAMPLES

In the following, the present invention will be described in detail by way of examples, however, it is to be noted that the present invention is not limited to these examples.

Example 1

Evaluation of Growth Ability Against Metabolic Analogue β-Ionone bacterium *Paracoccus* sp. strain TSN18E7 was inoculated in 5 mL of liquid medium shown in Table 1, and cultured for one (1) day at 25° C. under shaking and 150 rpm. The culture solution was diluted in a culture medium shown in Table 1, and spread on a plate culture medium having a composition shown in Table 2 supplemented with β-ionone (Aldrich) dissolved in dimethylsulfoxide (DMSO). β-ionone was supplemented at final concentrations of 0.01, 1, 2, 5 and 10 mM. Then the plate culture medium on which strain TSN18E7 was spread was cultured for 5 days at 25° C. Appearing colonies were visually counted and evaluated for growth ability of strain TSN18E7 for each concentration of β-ionone. The strain TSN18E7 inhibited growth in the presence of β-ionone of 1 mM or more, and formation of colony was not observed. We concluded that for separation of β-ionone resistant strain, suitable β-ionone concentration in culture is 1 mM in final concentration.

TABLE 1

| Ingredients | Adding amount |
| --- | --- |
| Dipotassium phosphate | 3.6 g/L |
| Potassium phosphate | 1.4 g/L |
| Sodium chloride | 8.8 g/L |
| Magnesium sulfate heptahydrate | 0.73 g/L |
| Trypticase peptone | 2 g/L |
| Yeast extract | 1 g/L |
| Glucose (*) | 10 g/L |
| Ferrous sulfate heptahydrate (*) | 0.1 mM |

(*) Aqueous solution, added after separately sterilized

Example 2

Mutagenesis and Preparation of Excellent Bacterial Strain

As in Example 1, strain TSN18E7 was inoculated to 5 mL of culture medium shown in Table 1, and cultured in a tube for a day at 25° C. under shaking at 150 rpm. 1 mL of this culture solution was transferred to 1.5 mL Eppendorf tube, and centrifuged at 15,000 rpm for 10 minutes to collect bacterial cells. These bacterial cells were suspended 1 mL of 0.1 M potassium phosphate buffer (buffer A) at pH 7.0, added with 10 µL of 3 mg/mL of N-methyl-N'-nitro-N-nitrosoguanidine (hereinafter, abbreviated as NTG) in water, and left for 30 to 60 minutes. Following centrifugation and removal of supernatant, operation of resuspending in buffer A was repeated twice to remove NTG. Then bacterial cells were suspended in 0.5 mL of buffer A, inoculated into 3 mL of culture medium shown in Table 1 and cultured for 4 to 5 hours. The resultant culture solution was diluted appropriately, and the diluted culture solution was applied on a plate culture medium having a composition of Table 2 supplemented with β-ionone dissolved in DMSO at a final concentration of 1 mM, followed by culturing for 5 days at 25° C. A colony exhibiting strong red color was selected from the grown colonies, and cultured for 7 days in a culture medium having a composition of Table 1 at 25° C. under shaking at 100 rpm. This culture solution was temporally analyzed, and a bacterial strain with improved productivity of carotenoid was selected.

TABLE 2

| Ingredients | Adding amount |
| --- | --- |
| Dipotassium phosphate | 3.6 g/L |
| Potassium phosphate | 1.4 g/L |
| Sodium chloride | 8.8 g/L |
| Magnesium sulfate heptahydrate | 0.73 g/L |
| Trypticase peptone | 2 g/L |
| Yeast extract | 1 g/L |
| Agar | 15 g/L |
| Glucose (*) | 10 g/L |
| Calcium chloride dihydrate (*) | 0.6 mM |
| Ferrous sulfate heptahydrate (*) | 0.1 mM |

(*) Aqueous solution, added after separately sterilized

Example 3

Evaluation of Mutant Strain

The bacterial strain obtained in Example 2 was selected at random, and inoculated into 5 mL of culture solution shown in Table 1, and cultured for one (1) day at 25° C. Then 60 mL of culture medium having a composition of Table 1 was sterilized in a 100 mL Erlenmeyer flask equipped with baffle, and inoculated with 2 mL of culture solution cultured in the above. After culturing for 7 days at 25° C. under shaking (100 rpm), the culture solution was picked up as appropriate, and turbidity (OD 660 nm) and carotenoid amount were determined. Quantification was executed by putting 1 mL of culture solution into 1.5 mL Eppendorf tube, and obtaining a pellet of bacterial cells by centrifugation at 15,000 rpm for 5 minutes. The bacterial cells were then suspended in 20 µL of pure water, and added with 200 µL of dimethylformamide and 500 µL of acetone, and then shaken to extract carotenoids. After centrifuging the liquid extraction at 15,000 rpm for 5 minutes and removing the residue, various carotenoids were quantified by high performance liquid chromatography (hereinafter, abbreviated as "HPLC") using TSK gel—ODS80™ column (TOSOH). Separation of carotenoids was executed in the following manner. Using a 5:95 mixed solvent of pure water and methyl alcohol as solution A and a 7:3 mixed solvent of methyl alcohol and tetrahydrofuran as solution B, first solution A was passed through the column for 5 minutes at a flow rate of 1 mL/min, then solution A and solution B were passed at the same flow rate at a linear concentration gradient from solution A to solution B of 5 minutes to allow elution, and then solution B was passed for 5 minutes. The concentration of astaxanthin was determined by monitoring absorbance at 470 nm and calculating it from a calibration curve made from known concentrations of astaxanthin reagent (Sigma). After calculation, a production amount of astaxanthin was evaluated, and a novel mutant strain TSTT001 (deposition number: FERM P-20670) with improved production amount of carotenoids and improved growth ability was selected from the mutant strains.

Figure 1:
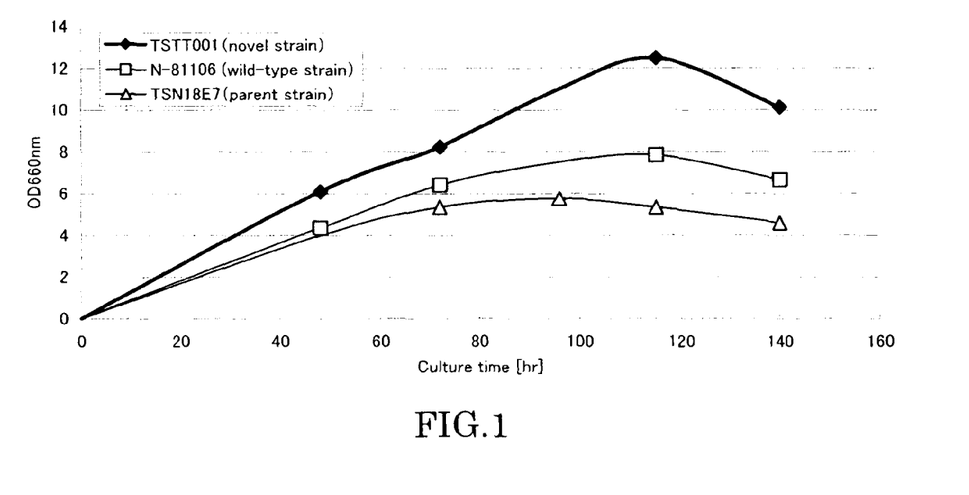
[FIG. 1] A graph showing temporal change of OD of the present bacterial strain, compared with strain N-81106 which is a wild-type strain, and strain TSN18E7 which is a parent strain.
Figure 2:
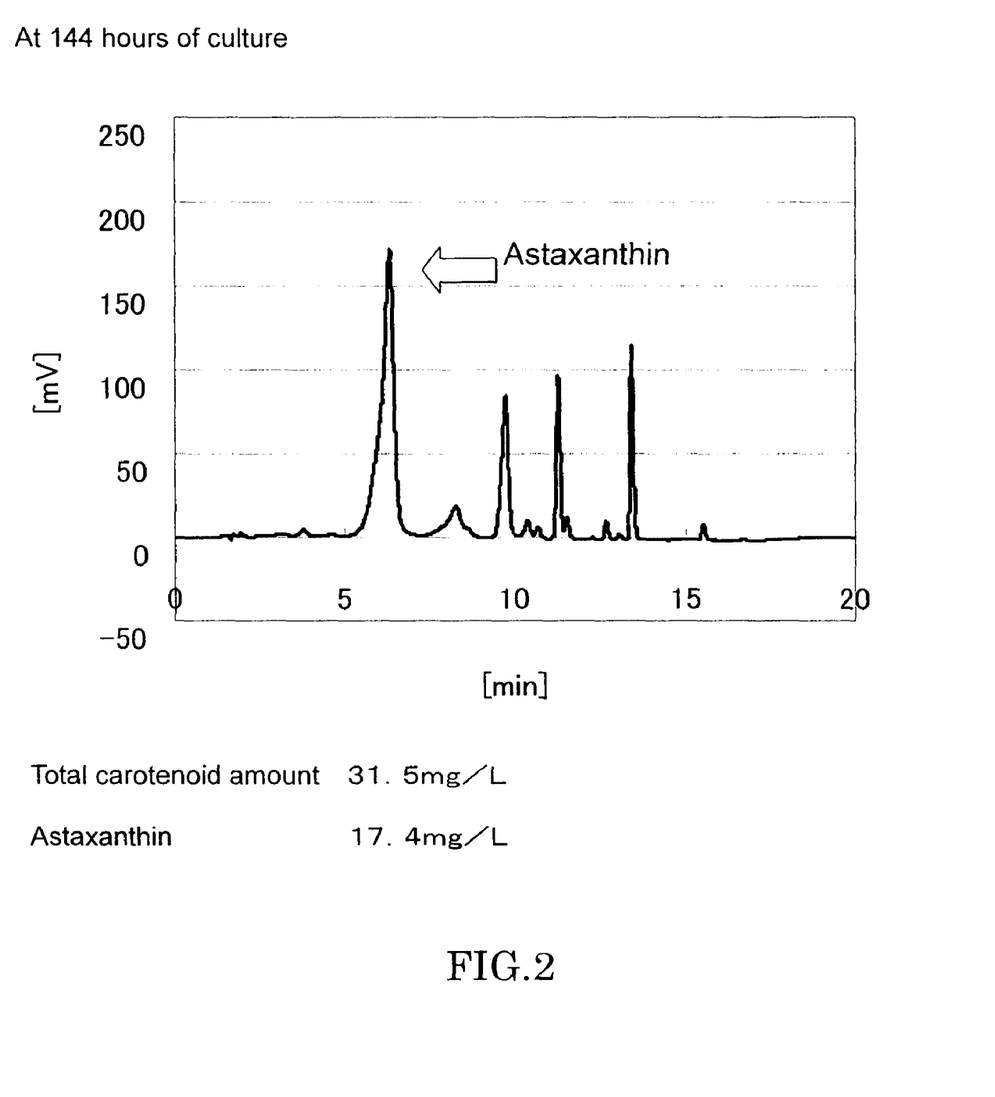
[FIG. 2] An HPLC chart showing generation pattern of carotenoid at 144 hours of culture.
Figure 3:
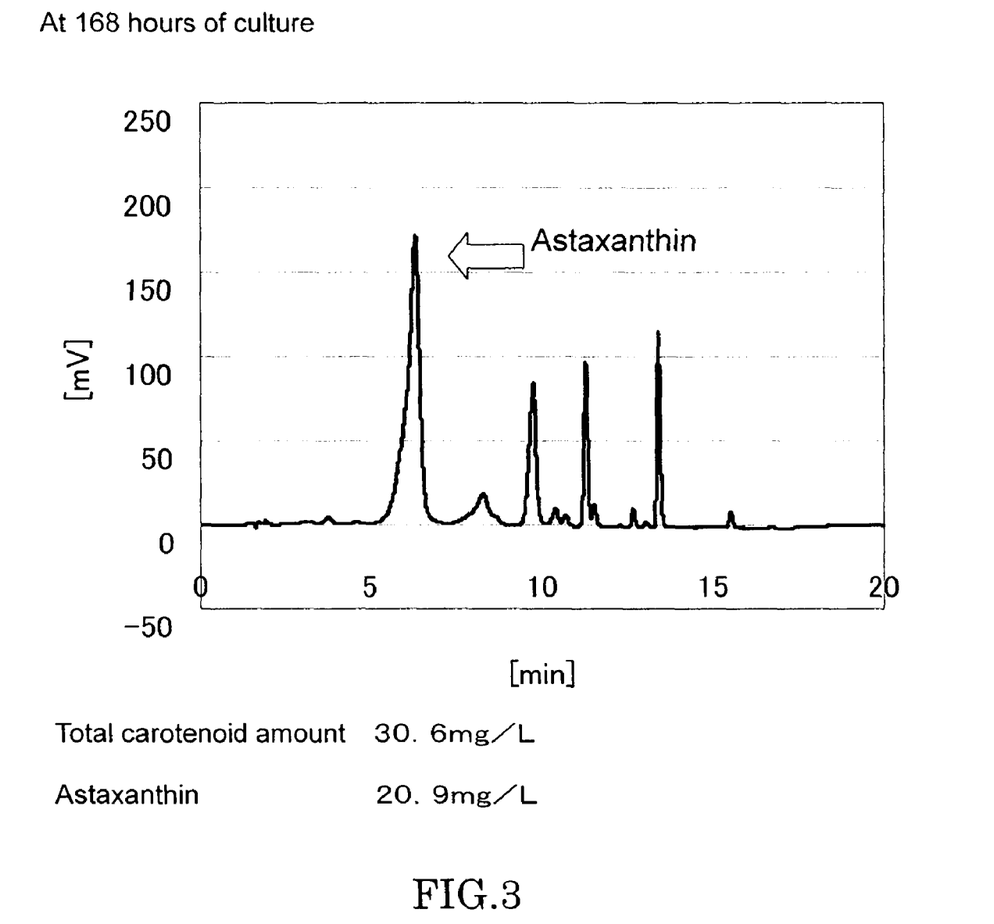
[FIG. 3] An HPLC chart showing generation pattern of carotenoid at 168 hours of culture.

FIG. 1 shows time courses of culture of strain N-81106, strain TSN18E7 which is a strain prior to mutagenesis, and strain TSTT001. The strain TSTT001 had an improved maximum OD value of about twice that of strain TSN18E7. Further, strain TSTT001 showed higher growth ability than strain N-81106 which is a wild-type strain. FIGS. 2 and 3 show carotenoid generating patterns (HPLC charts) at 144 hours and 168 hours of culture. Generation amounts of carotenoids can be determined from these HPLC charts. This experimental operation produced 20.9 mg at maximum of astaxanthin, and 31.5 mg at maximum of total carotenoid per 1 L of culture medium. The total carotenoids include astaxanthin, zeaxanthin, canthaxanthin, β-carotene, phoenicoxanthin and adonixanthin.

Example 4

Culturing of Novel Microorganism in Fermentation Tank and Quantification of Carotenoid Strain TSTT001 inoculated to 300 mL of culture medium shown in Table 3 was cultured for one (1) day at 25° C. under shaking at 100 rpm in a 500-mL Erlenmeyer flask equipped with baffle, and the culture solution was taken as a pre-pre-culture solution. Then 3 mL of the pre-pre-culture solution was inoculated to 100 mL of culture medium shown in Table 4 and cultured for one (1) day at 25° C. under shaking at 100 rpm in a 500-mL Erlenmeyer flask equipped with baffle. This culture solution was taken as a pre-culture solution. Then 3.0 L of culture medium shown in Table 5 was put into a fermentation tank having an entire capacity of 5.0 L (ABLE), sterilized at 121° C. for 20 minutes, and then 40 mL of the obtained pre-culture solution was inoculated and cultured for about 120 hours. Operation of fermentation tank was conducted in the following manner. First, temperature and pH of the fermentation tank were set at 22° C. and 7.0 to 7.2, respectively, and pH was adjusted by appropriately adding 2N sodium hydroxide and 15% aqueous ammonium. Stirring rate of the fermentation tank was set at 300 rpm at the start of culture, and gradually increased as the culture proceeds, and increased up to 370 rpm at 120 hours of culture. Shortage of carbon source occurring during culture process was compensated by appropriately adding 60% glucose. Glucose concentration was set at 10 g/L at the start of culture, and after it lowered to 5 g/L or less, glucose addition was started to adjust the concentration at 0.5 to 5 g/L.

TABLE 3

| Ingredients | Adding amount |
| --- | --- |
| Dipotassium phosphate | 3.6 g/L |
| Potassium phosphate | 1.2 g/L |
| Sodium chloride | 8 g/L |
| Peptone | 2 g/L |
| Yeast extract | 1 g/L |
| Glucose (*) | 5 g/L |
| Magnesium sulfate heptahydrate (*) | 3 mM |
| Calcium chloride dehydrate (*) | 0.2 mM |
| Ferrous sulfate heptahydrate (*) | 0.1 mM |

(*) Aqueous solution, added after separately sterilized

TABLE 4

| Ingredients | Adding amount |
| --- | --- |
| Dipotassium phosphate | 0.72 g/L |
| Potassium phosphate | 0.24 g/L |
| Sodium chloride | 8 g/L |
| Ammonium chloride | 2.5 g/L |
| Yeast extract | 5 g/L |
| Glucose (*) | 5 g/L |
| Magnesium sulfate heptahydrate (*) | 3 mM |
| Calcium chloride dehydrate (*) | 0.2 mM |
| Ferrous sulfate heptahydrate (*) | 0.1 mM |

(*) Aqueous solution, added after separately sterilized

TABLE 5

| Ingredients | Adding amount |
| --- | --- |
| Disodium phosphate 12H$_2$O | 4.44 g/L |
| Sodium phosphate dihydrate | 0.84 g/L |
| Ammonium sulfate | 2.76 g/L |
| Yeast extract | 9 g/L |
| Glucose (*) | 10 g/L |
| Magnesium sulfate heptahydrate (*) | 9 mM |
| Calcium chloride dehydrate (*) | 0.9 mM |
| Ferrous sulfate heptahydrate (*) | 2.1 mM |
| Zinc sulfate heptahydrate (*) | 0.135 mM |
| Manganese (II) chloride tetrahydrate (*) | 0.006 mM |
| Copper (II) chloride dihydrate (*) | 0.012 mM |

(*) Aqueous solution, added after separately sterilized

Figure 4:
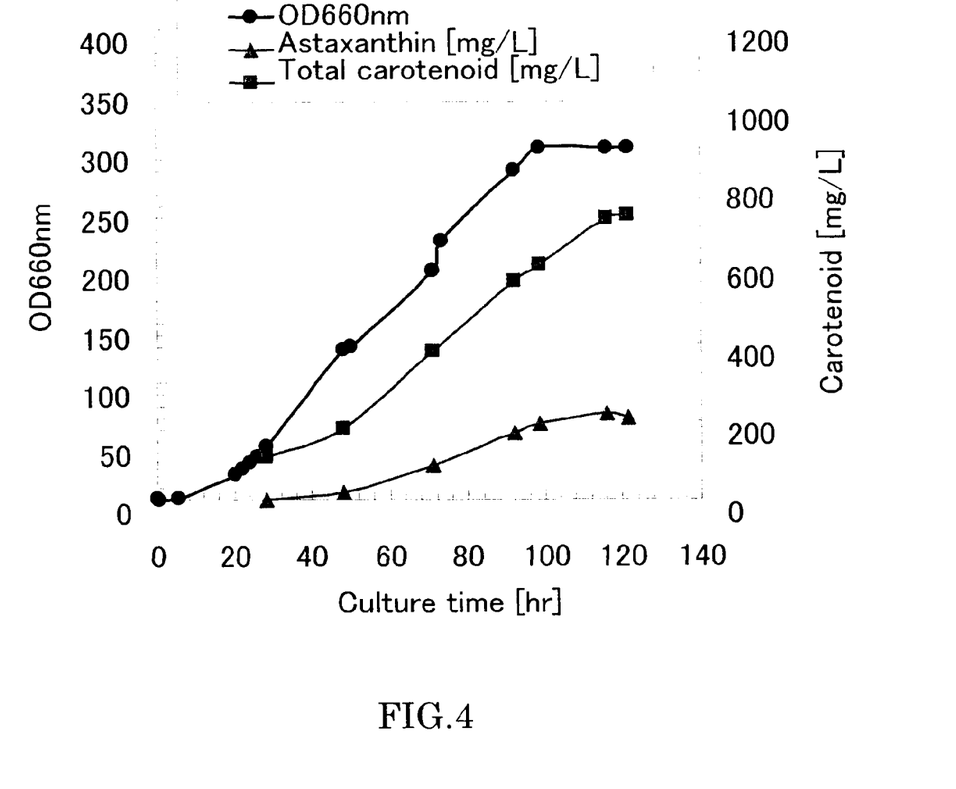
[FIG. 4] A graph showing temporal changes of astaxanthin generation amount and total carotenoid generation amount.

FIG. 4 shows temporal changes of OD, generation amount of astaxanthin and production amount of total carotenoid. As shown in the drawing, production amounts of total carotenoid and astaxanthin increase with the elapse time of culture, and Table 6 shows quantification results of different carotenoids at 120 hours of culture. In this experimental operation, 250 mg of astaxanthin, and 720 mg of carotenoid were produced per 1 L of culture medium.

TABLE 6

| | |
| --- | --- |
| Astaxanthin glycoside | 6 mg |
| Astaxanthin | 250 mg |
| Adonixanthin | 69 mg |
| Phoenicoxanthin | 132 mg |
| Canthaxanthin | 91 mg |
| Echinenone | 153 mg |
| β-carotene | 19 mg |
| Total (Total carotenoid) | 720 mg |

Example 5

Mutagenesis on Bacterium *Paracoccus* sp. Strain TSTT001 and Preparation of Excellent Bacterial Strain As in Example 1, strain TSTT001 was inoculated to 5 mL of culture medium shown in Table 1, and cultured in a tube for one (1) day at 25° C. under shaking at 150 rpm. 1 mL of this culture solution was transferred to 1.5 mL Eppendorf tube, and centrifuged at 15,000 rpm for 10 minutes to collect bacterial cells. These bacterial cells were suspended 1 mL of 0.1 M potassium phosphate buffer (buffer A) at pH 7.0, added with 10 μL of 3 mg/mL of N-methyl-N'-nitro-N-nitrosoguanidine (hereinafter, abbreviated as NTG) in water, and left for 30 to 60 minutes. Following centrifugation and removal of supernatant, operation of resuspending in buffer A was repeated twice to remove NTG. Then bacterial cells were suspended in 0.5 mL of buffer A, inoculated into 3 mL of culture medium shown in Table 1 and cultured for 4 to 5 hours. The resultant culture solution was diluted appropriately, and the diluted culture solution was applied on a plate culture medium having a composition of Table 2, followed by culturing for 5 days at 25° C. A colony exhibiting strong red color was selected from the grown colonies, and cultured for 7 days in a culture medium having a composition of Table 1 at 25° C. under shaking at 100 rpm. This culture solution was temporally analyzed, and a bacterial strain with improved productivity of carotenoid was selected.

As in Example 3, a production amount of carotenoid such as astaxanthin was evaluated, and strain TSTT031 (deposition number: FERM P-20689) and strain TSTT052 (deposition number: FERM P-20690) were obtained from mutant strains having improved productivity, compared with TSTT001 strain. Table 7 shows production amounts of carotenoids such as astaxanthin after completion of culture. As shown in Table 7, the strain TSTT031 and the strain TSTT052 are excellent strains having significantly higher productivity of carotenoids such as astaxanthin compared with the parent strain TSTT001.

TABLE 7

| Strain name | Turbidity (OD660 nm) | Astaxanthin (mg/L) | Total carotenoid (mg/L) |
| --- | --- | --- | --- |
| TSTT001 | 10.5 | 20.9 | 30.6 |
| TSTT031 | 11.5 | 23.2 | 50.4 |
| TSTT052 | 13.1 | 42.0 | 60.3 |

Example 6

Feeding Culture while Keeping Glucose Concentration at 0 to 6 g/L by Controlling Glucose Feeding Amount in Proportion to Concentration of Carbon Dioxide in Culturing of TSTT052

300 mL of culture medium having a composition shown in Table 8 was put into a 500 mL Erlenmeyer flask equipped with baffle, and sterilized at 121° C. for 20 minutes, and then inoculated with strain TSTT052 (deposition number: deposited under the name of FERM-20690) which is one of mutant strains of strain N-81106, and pre-pre-cultured at a shaking rate of 100 rpm for one (1) day at 25° C.

TABLE 8

| Ingredients | Adding amount |
| --- | --- |
| Dipotassium phosphate | 3.6 g/L |
| Potassium phosphate | 1.2 g/L |
| Glucose | 5 g/L |
| Sodium chloride | 8 g/L |
| Peptone | 2 g/L |
| Yeast extract | 1 g/L |
| Magnesium sulfate heptahydrate | 3 mM |
| Calcium chloride dihydrate | 0.2 mM |
| Ferrous sulfate heptahydrate | 0.1 mM |

Next, 100 mL of culture medium having a composition shown in Table 9 was put into a 500 mL Erlenmeyer flask equipped with baffle, and sterilized at 121° C. for 20 minutes, and then inoculated with mL of the above culture solution and pre-cultured at a shaking rate of 100 rpm for 18 hours at 25° C.

TABLE 9

| Ingredients | Adding amount |
| --- | --- |
| Dipotassium phosphate | 3.6 g/L |
| Potassium phosphate | 1.2 g/L |
| Glucose | 5 g/L |
| Sodium chloride | 8 g/L |
| Ammonium chloride | 2.5 g/L |
| Yeast extract | 2.5 g/L |
| Magnesium sulfate heptahydrate | 3 mM |
| Calcium chloride dihydrate | 0.2 mM |
| Ferrous sulfate heptahydrate | 0.1 mM |

Further, about 1.4 L of culture medium having a composition shown in Table 10 excluding glucose and metal salt was put into a 3 L fermentation tank, sterilized for 20 minutes at 121° C., and replenished with glucose and metal salt, and main culturing was started after addition of 90 mL of the culture solution of pre-culture. The culture temperature was 22° C., and pH was set in a range of from 7.0 to 7.4. Since pH decreases as the microorganism grows during culture, it was controlled to a predetermined range by addition of 10% ammonia water. Also aeration was effected at a rate of 1.8 L/min. For feeding a carbon source, 700 g/L of glucose was used. As a culturing device, BMS-03PI from ABLE was used, and as a discharged gas analyzer, DEX-2562 from ABLE was used.

TABLE 10

| Ingredients | Adding amount |
| --- | --- |
| Disodium phosphate 12H$_2$O | 4.44 g/L |
| Sodium phosphate dihydrate | 0.94 g/L |
| Glucose | 3 g/L |
| Ammonium sulfate | 2.76 g/L |
| Yeast extract | 9 g/L |
| Magnesium sulfate heptahydrate | 9 mM |
| Calcium chloride dihydrate | 0.9 mM |
| Ferrous sulfate heptahydrate | 2.1 mM |
| Zinc sulfate heptahydrate | 0.135 mM |
| Manganese chloride tetrahydrate | 0.006 mM |
| Copper chloride dihydrate | 0.012 mM |

Figure 5:
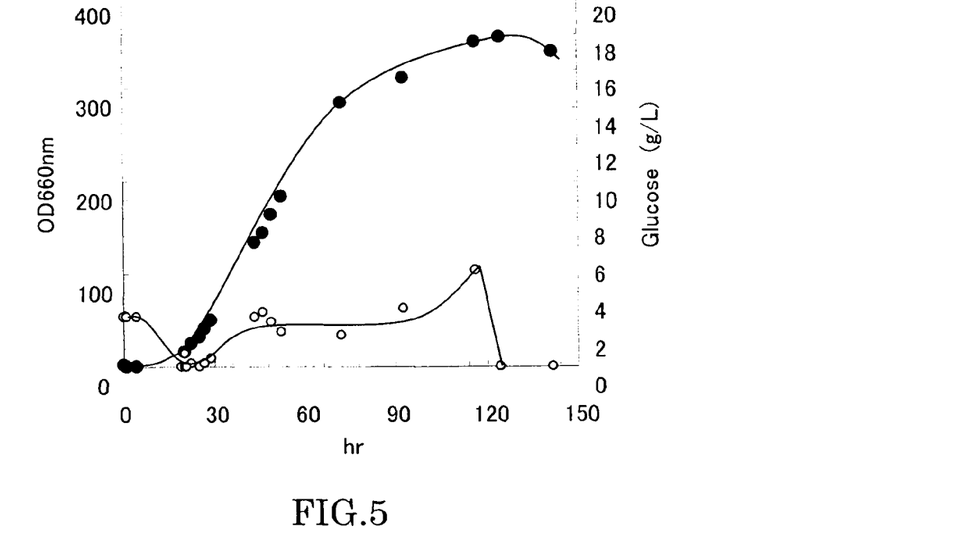
[FIG. 5] A view showing growth of microorganism and glucose concentration in a culture pattern in which the glucose concentration is automatically controlled to 0 to 6 g/L, wherein X axis (horizontal axis) represents time (unit: hour), and in Y axis (vertical axis), a closed circle represents the absorbance at 660 nm (unit: any unit) showing growth of microorganism, and an open circle represents the glucose concentration (unit: g/L).

In order to keep glucose concentration, a feeding pump was intermittently operated based on the feeding formula (1) using a culture control program of ABLE through a personal computer. For feeding, a quantification pump 101U (low-flow rate type) from Watoson-Marlow was used, and flow rate was set at 0.3 g/min. Further, the value of A in the formula (1) was set at 9.5 for the period from starting to 48 hours of culture, and at 8.0 for the subsequent period. During culture, glucose concentration was measured at regular intervals using a glucose analyzer (apparatus name: 2700 from YSI). Growth of microorganism was monitored by turbidity at 660 nm of culture solution. At 120 hours of culture, turbidity of culture solution reached 360. From a correlation equation between turbidity and cell density previously determined, bacterial cell yield was determined as 90 g/L. Further, glucose concentration was kept at about 3 g/L over the period of culture, however, since the tendency of accumulating at about 5 g/L was observed at 120 hours, the feeding was suspended at this point of time, and then feeding was restored after glucose was consumed to 0 g/L. The result of this culturing is shown in FIG. 5.

Figure 6:
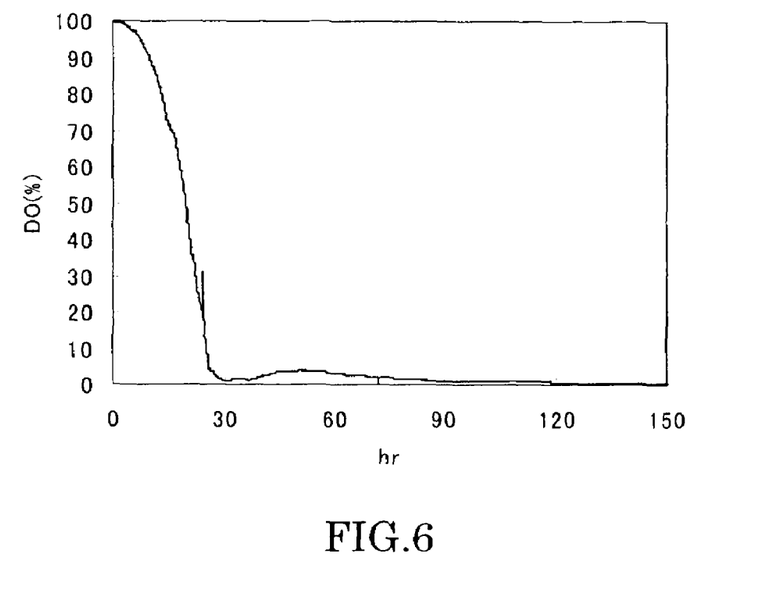
[FIG. 6] A view showing dissolved oxygen concentration in a culture pattern in which the glucose concentration is automatically controlled to 0 to 6 g/L, wherein X axis (horizontal axis) represents time (unit: hour), and Y axis (vertical axis) represents the dissolved oxygen concentration (DO) (unit: % by volume).

During the period from 24 hours of culture to end of culture, dissolved oxygen concentration was kept at about 0% saturation (FIG. 6). This reveals that glucose was maintained in culture without being depleted.

Figure 7:
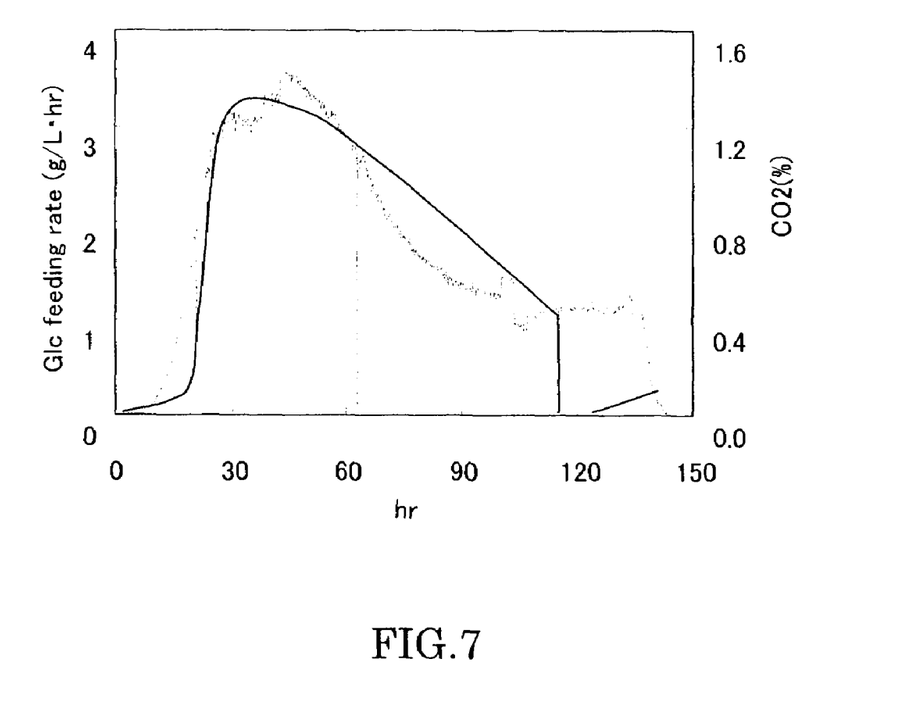
[FIG. 7] A view showing carbon dioxide gas concentration in outlet gas and glucose feeding rate in a culture pattern in which the glucose concentration is automatically controlled to 0 to 6 g/L, wherein X axis (horizontal axis) represents time (unit: hour), and in Y axis (vertical axis), the solid line (lower one in the drawing) represents the glucose feeding rate (unit: g/L·hr), and the broken line (upper one in the drawing) represents the carbon dioxide gas concentration (unit: % by volume).
Figure 8:
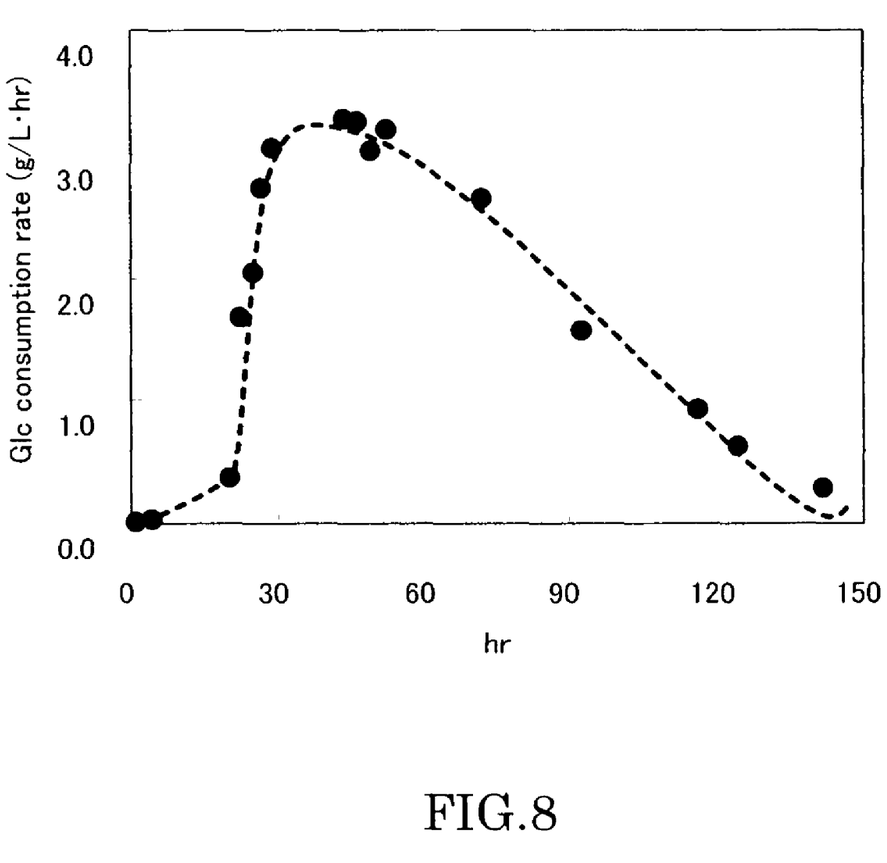
[FIG. 8] A view showing glucose consumption rate in a culture pattern in which the glucose concentration is automatically controlled to 0 to 6 g/L, wherein X axis (horizontal axis) represents time (unit: hour), and in Y axis (vertical axis), a closed circle represents the glucose consumption rate (unit: g/L·hr), and the broken line represents a real glucose consumption rate (unit: g/L·hr) estimated from distribution of the closed circles.

FIG. 7 shows transition of carbon dioxide gas concentration in outlet gas and feeding rate during a culturing period. Here, the feeding rate is shown by an average flow rate during 5 minutes. Feeding rate matched well with transition of $CO_2$ concentration. FIG. 8 shows transition of consumption rate of glucose. Transition of glucose feeding rate matched well with transition of consumption rate. From this result and transition of glucose concentration shown in FIG. 3, efficacy of glucose concentration control according to the present method was confirmed.

Analysis of generation amount of carotenoids after completion of culturing showed generation of 538 mg of astaxanthin, adonixanthin (69 mg), phoenicoxanthin (361 mg), canthaxanthin (261 mg), echinenone (119 mg) and β-carotene (7 mg) per 1 L of culture solution. Other carotenoids that are estimated as zeaxanthin was detected, however the amount was too small to be identified and quantified. Production amount of total carotenoid which is the sum of these carotenoids was 1320 mg per 1 L of culture solution. Analysis of organic acid generation amount in the culture supernatant resulted in detection of only 0.03 g/L of lactic acid.

In brief, by starting culture in the presence of glucose of 6 g/L or less, culturing while feeding high concentration of glucose from outside of the culturing device, and controlling the feeding rate so that it is proportion to concentration of carbon dioxide gas in the outlet gas in culture of strain TSTT052 which is a novel bacterial strain of the present invention, it is possible to keep the glucose concentration constant because glucose can be fed in coordination with the change in glucose consumption rate during culture. As a result, it is possible produce carotenoids such as astaxanthin at high yield while avoiding production inhibition by excess glucose as is the case of Comparative example below.

Comparative Example 1

Batch Culture with High Concentration of Glucose (130 g/L)

Figure 9:
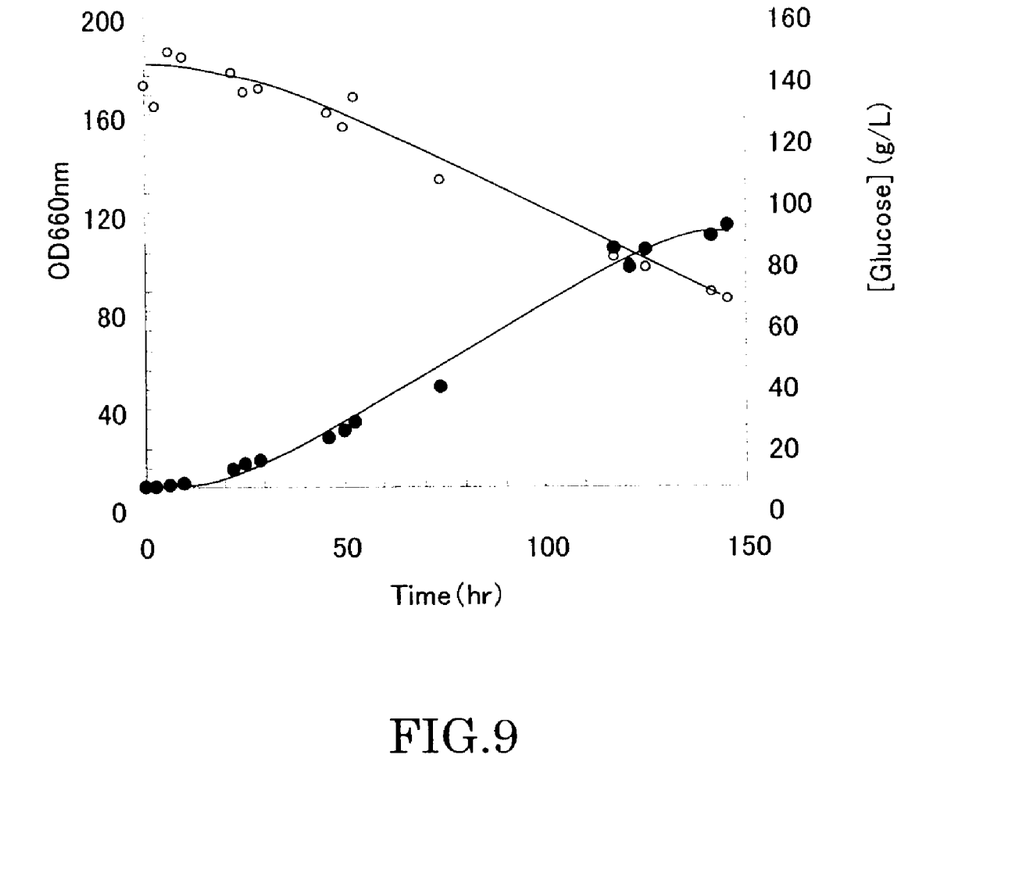
[FIG. 9] A view showing growth of microorganism and glucose concentration in a culture pattern of batch culture at high concentration (130 g/L) of glucose, wherein X axis (horizontal axis) represents time (unit: hour), and in Y axis (vertical axis), a closed circle represents the absorbance at 660 nm (unit: any unit) showing growth of microorganism, and an open circle represents the glucose concentration (unit: g/L).
Figure 10:
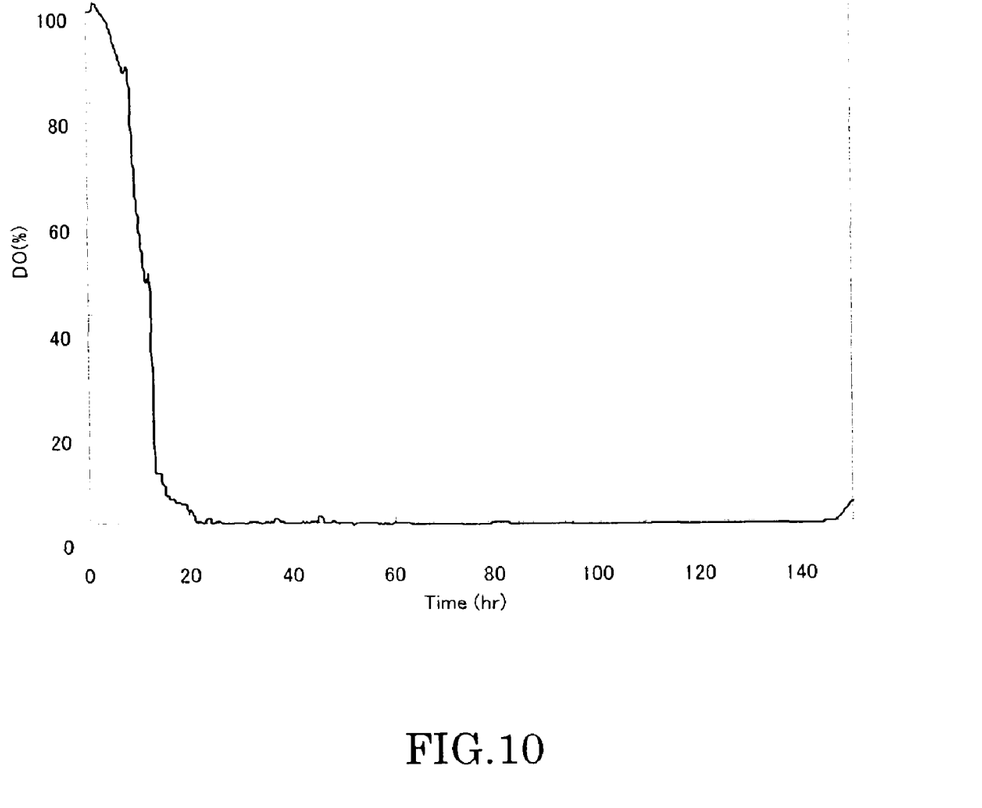
[FIG. 10] A view showing dissolved oxygen concentration in batch culture, wherein X axis (horizontal axis) represents time (unit: hour), and Y axis (vertical axis) represents the dissolved oxygen concentration (DO) (unit: % by volume).

Culturing was conducted similarly to Example 6 except that the glucose concentration at the start of culturing was 130 g/L and feeding was not effected. Transitions of growth of microorganism and glucose concentration in this case are shown in FIG. 9, and transition of dissolved oxygen concentration is shown in FIG. 10. The growth rate significantly decreased, and turbidity after 150 hours of culturing was about 100 (corresponding to 25 g/L of dry bacterial cells). Production amount of astaxanthin was 75 m g/L, and only phoenicoxanthin (91 m g/L), canthaxanthin (67 m g/L), echinenone (58 m g/L) were detected in low yields. In the culture solution, about 1 g/L of tartaric acid accumulated as a byproduct. These results revealed that high concentration of glucose not only inhibits growth of the present microorganism and production of carotenoids, but also promotes generation of organic acid which impairs quality of product. In other words, efficacy of culturing while keeping the glucose concentration at low level according to the method described herein was confirmed.

Example 7

Feeding Culture while Keeping Glucose Concentration at 0 to 6 g/L by Controlling Feeding Amount of Glucose in Proportion to Carbon Dioxide Gas Concentration in Culturing of Native Strain Culturing was conducted in a similar manner as in Example 3 except that wild-type strain (N-81106) was used. Turbidity at 660 nm after 80 hours of culture was 150 (corresponding to 50 g/L of dry bacterial cell). Production amounts of carotenoids were 52 g/L of astaxanthin, 48 g/L of adonixanthin, 5 g/L of phoenicoxanthin, 4 g/L of canthaxanthin, and 2 g/L of echinenone. Glucose concentration of culture solution was kept between 0 and 6 g by the similar method as in Example 3. The productivity of wild-type strain was poor compared with Example 3, which demonstrated significantly high carotenoid productivity of strain TSTT052 which is a novel bacterial strain of the present invention.

However, in comparison with the case where a wild-type strain is batch cultured in the presence of high concentration of glucose as shown in Comparative example 2 below, the carotenoid productivity was 1.6 times higher. That is, it was demonstrated that productivity is improved by keeping glucose concentration at 0 to 6 g/L according to the method of the present invention even in culturing of wild-type strain.

Comparative Example 2

Batch Culture of Wild-Type Strain

Using a wild-type strain (N-81106), culturing was conducted similarly to Comparative example 1 except that glucose concentration was 50 g/L. After 80 hours culturing, the turbidity at 660 nm was as small as 90 (corresponding to 30 g/L of dry bacterial cells). Production amounts of carotenoids were 29 g/L of astaxanthin, 22 g/L of adonixanthin, 2 g/L of phenicoxanthin, 3 g/L of canthaxanthin, and 1 g/L of equinenone. It was confirmed that also in a wild-type strain, high concentration of glucose inhibits not only growth but also production of carotenoids. In other words, it was confirmed that productivity was improved in a wild-type strain by applying the feeding method described herein, although not to the extent realized by strain TSTT052.

INDUSTRIAL APPLICABILITY

According to the present invention, it becomes possible to efficiently produce carotenoids such as astaxanthin. Carotenoids such as astaxanthin are useful as pigments for feed and food, and antioxidants.

The invention claimed is:

1. A microorganism that produces at least 720 mg of carotenoids per liter of culture medium wherein the microorganism is obtained by breeding wild type *Paracoccus* bacteria that produces carotenoids wherein said bacterium is strain TSTT052.

2. A microorganism that produces at least 250 mg of astaxanthin per liter of culture medium wherein the microorganism is obtained by breeding wild type *Paracoccus* bacteria that produces carotenoids wherein said bacterium is strain TSTT052.

3. The microorganism of claim 1 wherein said breeding comprises treating wild type *Paracoccus* bacteria with N-methyl-N'-nitro-N-nitrosoguanidine, ethyl methane sulfonate (NTG) in a liquid culture, followed by growth of said bacteria on a plate comprising an increasing concentration of a metabolic analogue of carotenoids and selecting a strain that produces at least 720 mg/liter of carotenoids.

4. A method of producing carotenoids comprising culturing the microorganism according to claim 2 in a culture solution.

5. The method of producing carotenoids according to claim 4, wherein the microorganism is *Paracoccus* sp. strain TSTT052.

6. The method of producing carotenoids according to claim 4, wherein the culture solution is has a concentration of carbon source at 10 g/L or less.

7. The method of producing carotenoids according to claim 4, comprising maintaining the concentration of carbon source in the culture solution at a concentration that does not cause depletion of carbon source in any stage of culturing.

8. The method of producing carotenoids according to claim 7, wherein depletion of carbon source occurs at a concentration of carbon source of 0 g/L, and is a condition that is associated with deterioration of respiration activity of the microorganism being cultured.

9. The method of producing carotenoids according to claim 4, further comprising measuring the amount of carbon dioxide gas generated from the culture solution, and controlling the amount of carbon source based on the amount of carbon dioxide gas generated to keep the concentration of carbon source constant during culturing.

10. The microorganism of claim 1 wherein said breeding comprises treating wild type *Paracoccus* bacteria with N-methyl-N'-nitro-N-nitrosoguanidine, ethyl methane sulfonate (NTG) in a liquid culture followed by growth of said bacteria on a plate comprising an increasing concentration of a metabolic analogue of carotenoids and selecting a strain that produces at least 250 mg/liter of astaxanthin.

* * * * *